United States Patent [19]

Comai

[11] Patent Number: 4,769,061

[45] Date of Patent: * Sep. 6, 1988

[54] INHIBITION RESISTANT 5-ENOLPYRUVYL-3-PHOSPHOSHIKIMATE SYNTHASE, PRODUCTION AND USE

[75] Inventor: Luca Comai, Davis, Calif.

[73] Assignee: Calgene Inc., Davis, Calif.

[*] Notice: The portion of the term of this patent subsequent to Aug. 13, 2002 has been disclaimed.

[21] Appl. No.: 697,808

[22] Filed: Feb. 4, 1985

Related U.S. Application Data

[63] Continuation-in-part of Ser. No. 455,634, Jan. 5, 1983, Pat. No. 4,535,060.

[51] Int. Cl.⁴ .................... A01N 57/00; A01N 43/02; A01N 43/18; A01N 43/64; A01N 37/10; A01N 37/36; A01N 37/38; A01N 37/10; A01N 37/38; A01N 37/18; C12N 5/00; C12N 15/00; C12N 9/10

[52] U.S. Cl. .......................................... 71/86; 71/91; 71/92; 71/93; 71/107; 71/108; 71/109; 71/110; 71/115; 71/116; 71/117; 71/118; 800/1; 435/172.3; 435/193; 435/240.4; 935/14; 935/67; 935/64

[58] Field of Search .................... 435/91, 172.1, 172.2, 435/172.3, 183, 193, 232, 240, 253, 879, 317, 240.4; 536/27; 935/14, 64, 67, 111; 47/58; 71/86, 91, 93, 92, 106, 105, 108, 107, 109, 110, 116, 118, 117, 115; 800/1

[56] References Cited

U.S. PATENT DOCUMENTS

| | | | |
|---|---|---|---|
| 4,237,224 | 12/1980 | Cowen et al. | 435/172.3 |
| 4,278,765 | 7/1981 | Debabou et al. | 435/172.3 |
| 4,407,956 | 10/1983 | Howell | 435/317 |
| 4,443,971 | 4/1984 | Chaleff | 47/58 |
| 4,459,355 | 7/1984 | Cello et al. | 435/172.3 |
| 4,535,060 | 8/1985 | Comai | 435/317 X |

FOREIGN PATENT DOCUMENTS 0035831  9/1981  European Pat. Off. ............ 435/172

OTHER PUBLICATIONS

Rogers, S. G. et al., *App & Envir Microb.*, vol. 46, No. 1, pp. 37–43, Jul. 1983.
Comai, L. et al., *Science*, vol. 221, pp. 370–371, 1983.
Meyers, et al., *J. Bact*, vol. 124(3) pp. 1227–1235, 1975.
Roisch et al., Hoppe-Seyler–s Zeits. for Phys. Chem, vol. 361(7) pp. 1049–1058), 1980.
*Genetic Maps*, vol. 2, Stephen J. OBrin (Ed), Jun. 1982, pp. 108–121.
Biochem. of Bact. Growth (Mandelstam et al.–Eds) pp. 278–282, 1982.

*Primary Examiner*—Thomas G. Wiseman
*Assistant Examiner*—Jayme A. Huleatt
*Attorney, Agent, or Firm*—Bertram Rowland

[57] ABSTRACT

Enhanced resistance to glyphosate, an inhibitor of the aromatic amino acid biosynthesis pathway, is imparted to a glyphosate sensitive host. A mutated aroA gene is employed which expresses 5-enolpyruvyl-3- phosphoshikimate synthase (EC: 2.5.1.19) (ES-3-P synthase). Methods are provided for obtaining the aroA mutation which provides the enzyme resistant to inhibition by glyphosate, means for introducing the structural gene into a sensitive host, as well as providing a method of producing the enzyme.

The *E. coli* strain C600(pPMG1) has been deposited at the A.T.C.C. on Dec. 14, 1982 and given A.T.C.C. Accession No. 39256.

12 Claims, No Drawings

INHIBITION RESISTANT 5-ENOLPYRUVYL-3-PHOSPHOSHIKIMATE SYNTHASE, PRODUCTION AND USE

BACKGROUND OF THE INVENTION

1. Field of the Invention

Hybrid DNA technology provides new opportunities for preparing a wide variety of novel compounds having enhanced or unique properties. Cellular life is dependent upon the ability to perform enzyme reactions which provide energy for the cell and produce components essential to the cell's viability. Where a number of cells coexist in relative proximity, it has been frequently of interest to be able to select for one group of cells as against the other group of cells. This mode of selection has found extensive use in hybrid DNA technology in selecting for transformants and transductants.

For the most part, antibiotic resistance has been employed as a marker which is introduced into the cell in conjunction with one or more other structural genes of interest. There are numerous other situations, where one is interested in selecting for cells, where a group of cells is undesired. Coming within such categories are such diverse situations as oncogenesis, where one wishes to selectively destroy tumor cells, in the use of herbicides, where one wishes to select for a crop plant as against a weed, and in therapy against pathogens, where one wishes to destroy an invading microorganism while having minimal effect on the host. The opportunity to introduce DNA in a form where it can express enhanced resistance to a biocidal agent permits one to use enhanced amounts of the biocidal reagent while protecting the host against any detrimental effect from the biocide or biostat.

In those situations, where protection is afforded by producing an enzyme which is insensitive to the biocide or can destroy the biocide, the mutated gene affords a new product which can have a wide variety of useful properties. Enzymes can be used as labels, particularly in diagnostic assays, for the production of products, in assaying for substrates and inhibitors, purification, and the like. The ability to modify an enzyme's specificity can allow for the catalysis of reactions otherwise not available to the enzyme, enhanced activity of the enzyme, or enhanced selectivity of the enzyme.

2. Brief Description of the Prior Art

Hollander and Amrhein, *Plant Physiol.* (1980) 66:823-829; Amrhein et al., ibid. (1980) 66:830-834 and Steinruecken and Amrhein, *Biochem. Biophys. Res. Comm.* (1980) 94:1207-1212, report the biochemical characterization of a target site for glyphosate. This site was identified as a step of the shikimic acid pathway present in plants and bacteria in providing the precursor to aromatic amino acids. Transformation of plants employing Ti and Ri plasmids is described in Garfinkel, *J. Bacteriol.* (1980) 144:723; White, ibid (1980) 144:710; Herrera-Estrella, et al., *Nature* (1983) 303:209; Fraley et al. *Proc. Natl. Proc. Acad. Sci. USA* (1983) 80:4803; and Horsch et al., *Science* (1984) 223:496.

SUMMARY OF THE INVENTION

Novel DNA sequences and constructs are provided which can be used for expression of an enzyme in the shikimic acid pathway, which enzyme has reduced sensitivity to glyphosate. The sequences and constructs can be used for producing the enzyme, which finds use in a wide variety of applications as a label in assays and in the production of its normal product and in providing protection to a cellular host from glyphosate. Plant hosts can be made glyphosate-resistant, where the plant hosts include cells in culture, callus, seedlings and mature plants. A method is provided for producing the mutated enzyme.

DESCRIPTION OF SPECIFIC EMBODIMENTS

In accordance with the subject invention, DNA sequences are provided which express a glyphosate-resistant enzyme in the shikimic acid metabolic pathway, particularly the enzyme which catalyzes the conversion of phosphoenolpyruvate and 3-phosphoshikimic acid to 5-enolpyruvyl-3-phosphoshikimic acid. The enzyme is 5-enolpyruvyl-3-phosphoshikimate synthase (EC: 2. 5. 1. 19) (hereinafter referred to as "ES-3-P synthase"). The structural gene expresses an enzyme which is strongly resistant to glyphosate (N-phosphonomethyl glycine), so that the enzyme is active in the presence of significant amounts of glyphosate and can impart glyphosate resistance to a glyphosate sensitive cell in which the structural gene can be expressed. DNA constructs are provided which include the structural gene sequence for expression of the glyphosate-resistant ES-3-P synthase, which constructs may be introduced into a variety of hosts in a variety of ways and depending upon the nature of the construct and the host, may be present as an episomal element or integrated into the host chromosome.

The structural gene providing the glyphosate-resistant ES-3-P synthase can be obtained as a mutation in the aroA gene of a glyphosate sensitive organism. The organism may be mutagenized in a variety of ways, either physically or chemically, and mutants selected by their glyphosate resistance. In addition, mutants may be further selected by complementation of an aroA mutant, so as to change an aroA auxotroph to prototrophy.

The source of the aroA gene may be any organism which contains a functional aroA gene. The organism may be prokaryotic or eukaryotic, including bacteria, algae, plant cells, or the like. The source may be the intended host for the mutated glyphosate resistant gene or a different organism of the same or different species.

Prokaryotic sources have a number of advantages in allowing for a large number of mutations which may then be screened. Prokaryotes have a relatively small genome allowing for simpler isolation of the desired fragment. The use of a prokaryotic organism simplifies detection and manipulation of the aroA gene.

Illustrative prokaryotes and eukaryotes include bacteria such as Salmonella and Escherichia, fungi, such as Aspergillus, Neurospora and yeasts, plants, such as tobacco, petunia and soybean, algae, such as green and blue-green algae, etc., particularly cells which are glyphosate sensitive.

The source organisms are mutangenized and selected for glyphosate resistance as well as dependance of such resistance from a change in ES-3-P synthase. It may be desirable to screen the resulting mutagenized organisms and select those that show glyphosate resistance and subject them to further mutagenization and screening. In this manner, further enhancements in glyphosate resistance may be achieved. The resultant glyphosate-resistant organisms are then used to produce a genomic bank, where the intact structural gene may be obtained on fragments of 25Kb or less. Initially, the genomic bank is introduced into an appropriate host in which the cistron is capable of expression, so that glyphosate resistance may be selected for and the genomic fragment excised from the episomal element for further genetic manipulation to provide for a fragment less than about 5.5Kb containing the intact structural gene for ES-3-P synthase.

The large cloned genomic fragments may be randomly cleaved or cleaved using one or more restriction enzymes to provide fragments of from about 2 to 5Kb or less which may still include an intact cistron for ES-3-P synthase. The smaller fragments may be cloned and screened using probes complementary to a portion of the ES-3-P synthase coding region and/or screening the cloning vectors in an auxotrophic host for complementation to prototrophy in ES-3-P synthase and/or glyphosate resistant ES-3-P synthase competence.

Of particular interest are ES-3-P synthase enzymes which have been mutated in one or more amino acids in the amino acid 90–110 region, particularly where a neutral aliphatic amino acid has been substituted for a proline, more particularly where the substitution is oxy substituted, as in serine and theonine. (Neutral aliphatic amino acids include G, A, V, L, I, S, T, M, C). Preferably, the neutral aliphatic amino acid will be of from 3 to 5 carbon atoms. Within the 90–110 amino acid region, the region 100–102 is preferred, more preferably amino acid 101.

Thus, those aroA genes which have a proline in the 90–110 amino acid region and have undergone a mutation resulting in one or more transversions or transitions, so that a proline is substituted by a different amino acid resulting in glyphosate resistance, find use in this invention. Of particular interest is the *S. typhimurium* gene, which has proline replaced by serine at amino acid 101 of the enzyme.

The DNA sequence containing the structural gene expressing the glyphosate-resistant ES-3-P synthase may be joined to a wide variety of other DNA sequences for introduction into an appropriate host cell. The companion sequence will depend upon the nature of the host, the manner of introduction of the DNA sequence into the host, and whether episomal maintenance or integration is desired.

For prokaryotic hosts, a wide variety of vectors exist which may be used for introduction by transformation, conjugation, transduction or transfection of the DNA sequence into a prokaryotic host. DNA sequences include a wide variety of plasmids, such as pBR322, pACYC184, pMB9, pRK290, etc.; cosmids, such as pVK100; or virus, such as P22, etc.

For eukaryotic hosts, a wide variety of techniques may be employed for DNA introduction into the host, such as transformation with $Ca^{++}$-precipitated bare DNA, a plasmid or a minichromosome, or microinjection with a micropipette. Depending upon whether a competent replication system is present in the DNA construction, will determine whether the DNA may be replicated as an episomal element, or the DNA may be integrated into the host genome, and the structural gene expressed in the host. Episomal elements may be employed, such as tumor inducing plasmids, e.g., Ti, Ri or fragments thereof or viruses, e.g., CaMV, TMV or fragments thereof, which are not lethal to the host, and where the structural gene is present in such episomal elements in a manner allowing for expression of the structural gene. Particularly of interest are fragments having the replication function and lacking other functions such as oncogenesis, virulence, etc.

The first stage of the subject invention is the development of a DNA sequence which is capable of expressing a glyphosate-resistant protein which is capable of fulfilling the function of ES-3-P synthase. An appropriate source is employed which is glyphosate sensitive, can be grown in culture, and has the capability of expressing the ES-3-P synthase structural gene to provide the desired enzyme. It is not necessary that the host which is ultimately to be provided with glyphosate resistance be the same as the organism which is mutagenized. As already indicated, the glyphosate resistance may be provided by a gene present on a stable episomal element or a gene integrated into the host by a recombination event resulting in integration of the structural gene coding for the glyphosate-resistant ES-3-P synthase. Either prokaryotic or eukaryotic organisms may be employed for the mutagenesis, the source being chosen based on its glyphosate resistance, ease of selection, efficiency of growth, and utility of the mutagenized structural gene for use in the ultimate host.

Mutagenesis may be performed using chemical or physical mutagenic techniques or by genetic engineering techniques. The ES-3-P synthase gene to be mutagenized may be present in the chromosome or on an episomal element. Chemical mutagenic agents include ethyl methanesulfonate, diazo reagents, e.g. N-nitroso, N-methyl glycine, psoralens, etc. Physical mutagenic agents include ultraviolet light, X-rays, etc.

Genetic engineering techniques which may be used include in vitro mutagensis, employing a synthetic adapter in the region of interest which can be substituted into the gene, partial synthesis and ligation to the wild-type remainder of the gene, or the like.

Since the parent cell is glyphosate sensitive, selection can be carried out by selecting for glyphosate resistance. Glyphosate resistance may be as a result of a number of different types of changes in the cell and in order to ensure that the mutagen provides an enzyme which is glyphosate-resistant, it is necessary to establish that the mutation has occurred in the aroA gene. This can be achieved by employing cotransduction to an aroA auxotroph and selecting for glyphosate resistance and $aroA^+$ in *E. coli* or Salmonella or by other similar means or by isolating the expression product for example, by affinity chromatography and determining the enzyme activity and glyphosate resistance.

Cotransduction can be achieved with a wide variety of viruses (including phage) which are capable of transferring DNA from the genome of the host to another host in which the virus is temperate. In this manner, one can transduce a second host, employ an appropriate lysate, and select for the transduced host with glyphosate resistance, as well as aroA prototrophy. The resulting modified cells may now be mutagenized again or as many additional times as desired, repeating the transfers and selecting for continuously enhanced glyphosate resistance. Desirably, a host should be capable of multiplying in the presence of at least about 0.5 mg/ml of glyphosate, preferably in the presence of about 1 mg/ml glyphosate and even more preferred in the presence of at least 1.5 mg/ml glyphosate in a nutrient medium without the presence of aromatic amino acid in the nutrient medium.

When the desired level of glyphosate resistance has been achieved, the mutagenized aroA locus may be isolated and cloned. Depending upon the choice of restriction enzyme, either partial or complete digestion will be employed. Alternatively, one could initially isolate the gene from a genomic library by employing aroA complementation or other means of identification like immunological detection of the gene product or the use of a synthetic oligonucleotide probe deduced from the protein sequences. The gene could then be mutagenized as described above or by in vitro mutagenesis, changing one or more codons. The mutagenized gene may then be excised and gene fragments isolated.

The resulting fragments may then be cloned employing an appropriate cloning vector. Cloning can be carried out in an appropriate unicellular microorganism, e.g. a bacterium such as *E. coli*. Desirably, one may use a cosmid, where partial or complete digestion provides fragments having about the desired size. For example, the cosmid pVK100 may be partially digested with BglII and may be ligated to the fragments resulting from a Sau3A digestion of the genome of a glyphosate-resistant cell. Packaging will insure that only fragments of the desired size will be packaged and transduced into the host organism.

The host organism may be selected for glyphosate resistance and/or aroA+. The recipient strains may be modified to provide for appropriate genetic traits which allow for selection of transductants. In microorganisms, the transductants may be used for conjugation to other microorganisms, using a mobilizing plasmid as required. Various techniques may then be used for reducing the size of the fragment containing the structural gene for the glyphosate-resistant ES-3-P synthase. For example, the cosmid vector may be isolated, cleaved with a variety of restriction endonucleases, e.g. BglII, HindIII, etc., and the resulting fragments cloned in an appropriate vector, conveniently the cosmid vector previously used. A fragment of less than about 5.5Kb, usually less than about 5Kb, conveniently less than 2Kb, can be cloned and provide for aroA complementation and the glyphosate-resistant ES-3-P synthase.

The enzyme may be produced from any convenient source, either prokaryotic or eukaryotic. Where secretion is not obtained, the enzyme may be isolated by lysing the cells and isolating the ES-3-P synthase according to known ways. Useful ways include chromatography, electrophoresis, affinity chromatography, or the like. Conveniently, N-phosphonomethyl glycine may be conjugated through an appropriate functionality, e.g., the carboxyl group to an insoluble support and used as a packing for the isolation of the ES-3-P synthase.

The purified enzyme can be used in a wide variety of ways. It may be used directly in assays for phosphoenolpyruvate, 3-phosphoshikimic acid and for glyphosate. Alternatively, the subject enzyme can find use as a label in diagnostic assays, by being conjugated to an analyte of interest, e.g. a hapten or antigen, as such assays are described in U.S. Pat. Nos. 3,654,090; 3,817,837; and 3,850,752. The methods of conjugation, as well as the determination of the concentration of an analyte are described in extensive detail in these patents, and the appropriate portions of their disclosures are incorporated herein by reference.

The DNA sequence encoding for the glyphosate-resistant ES-3-P synthase may be used in a variety of ways. The DNA sequence may be used as a probe for isolation of wild type or mutated ES-3-P synthase Alternatively, the DNA sequence may be used for integration by recombination into a host to provide for imparting glyphosate resistance to the host.

With plant cells, the structural gene as part of a construction may be introduced into a plant cell nucleus by micropipette injection for integration by recombination into the host genome. Alternatively, temperate viruses may be employed into which the structural gene may be introduced for introduction into a plant host. Where the structural gene has been obtained from a source having regulatory signals which are not recognized by the plant host, it may be necessary to introduce the appropriate regulatory signals for expression. Where a virus or plasmid, e.g. tumor inducing plasmid, is employed and has been mapped, a restriction site can be chosen which is downstream from a promoter into which the structural gene may be inserted at the appropriate distance from the promoter. Where the DNA sequences do not provide an appropriate restriction site, one can chew back for various times with an exonuclease, such as Ba131 and insert a synthetic restriction endonuclease site. Methods for introducing viruses and plasmids into plants are amply described in the literature. (Matzke and Chilton, *J. Mol. App. Genetics* (1981) 1:39-49.)

Of particular interest is the use of a tumor-inducing plasmid, e.g., Ti or Ri, where the aroA gene may be integrated into plant cell chromosomes. Descriptions of the use of Ti-plasmids and Ri-plasmids may be found in PCT Publication Nos. WO84/02913, 02919 and 02920 and EPO Application No. 0 116 718. By employing the T-DNA right and left borders, where the borders flank a cassette comprising the aroA gene under transcriptional and translational regulatory signals recognized by the plant host, the cassette may be integrated into the plant genome and provide for expression of the glyphosate-resistant enzyme in the plant cell at various stages of differentiation.

As transcriptional and translational regulatory regions, conveniently opine promoter and terminator regions may be employed, which allow for constitutive expression of the aroA gene. Alternatively, other promoters and/or terminators may be employed, particularly promoters which provide for inducible expression or regulated expression in a plant host. Promoter regions which may be used from the Ti-plasmid include the octopine synthase promoter, nopaline synthase promoter, agropine synthase promoters, or the like. Other promoters include viral promoters, such as CaMV Region VI promoter or full length promoter, the promoters associated with the ribulose-1,5-bisphosphate carboxylate genes, e.g., the small subunit, genes associated with phaseolin, protein storage, cellulose formation, or the like.

The various sequences may be joined together in conventional ways. The promoter region may be identified by the region being 5' from the structural gene, for example, the opine gene, and by restriction mapping and sequencing may be selected and isolated. Similarly, the terminator region may be isolated as the region 3' from the structural gene. The sequences may be cloned and joined in the proper orientation to provide for constitutive expression of the aroA gene in a plant host.

By modifying crop plant cells by introduction of a functional gene expressing glyphosate-resistant ES-3-P synthase, one can use glyphosate as a herbicide with a wide variety of crops at concentrations which ensures the substantially complete or complete removal of weeds, while leaving the crop relatively unaffected. In this manner, substantial economies can be achieved in that fertilizers and water may be more efficiently utilized, and the detrimental effects resulting from the presence of weeds avoided.

The glyphosate-resistant enzyme may be introduced into a wide variety of plants, both monocotyledon and dicotyledon, including maize, wheat, soybean, tobacco, cotton, tomatoes, potatoes, Brassica species, rice, peanuts, petunia, sunflower, sugar beet, turfgrass, etc. The gene may be present in cells or plant parts including callus, roots, tubers, propagules, plantlets, seed, seedlings, pollen, or the like.

By providing for glyphosate-resistant plants, a wide variety of formulations may be employed for protecting crops from weeds. For example, for corn, glyphosate could be used by itself for post-emergent control of weeds, or alternatively, combination formulations could be employed. Combinations could be with an acetanilide herbicide such as alachlor or metalochlor, or Atrazine or cyanazine could also be used for early post-emergent control of weeds. Preferably, glyphosate would be used in conjunction with broadleaf herbicides, particularly 2,4-D type, such as dicamba, bromoxynil on, bentazon. Similarly, for soybean, tobacco, and cotton, glyphosate could be used alone for post-emergent control, while combination formulations, particularly glyphosate plus post-emergent broadleaf herbicides, such as bentazon, and aciflurofen, while for tomatoes, glyphosate plus aciflurofen would find use.

Conventional amounts of the pesticides would be used in the formulations to deliver from about 0.1 to 4 lb/acre, preferably 0.2 to 2 lb/acre, of glyphosate, where the other herbicide would be in amounts to deliver from about 0.1 to 4 lb/acre of active ingredient. Formulations would include other additives, such as detergents, adjuvants, spreading agents, sticking agents, stabilizing agents, or the like. The formulations may either be wet or dry formulations, including flowable powders, emulsifiable concentrates and liquid concentrates, as is known in the art.

The herbicidal solutions may be applied in accordance with conventional ways, for example, through spraying, irrigation, dusting, or the like.

The glyphosate resistant ES-3-P synthase will manifest its resistance by having a Ki/Km ratio (determined as described in the experimental section) for glyphosate/3-phosphoshikimic acid of at least 1.5, preferably at least 2, and more preferably at least 3 usually not exceeding 10, and a glyphosate/PEP ratio of greater than about 0.1, preferably greater than about 0.2, more preferably not greater than about 1.25, and usually not exceeding 1, more usually not exceeding 0.5.

Usually, the glyphosate resistant mutated ES-3-P synthase will have a specific activity at 28° C. at concentrations of from about 1-10 times Km for 3-phosphoshikimic acid of at least about twice for the mutated synthase. At a concentration of 10×Km of 3-phosphoshikimate and $5 \times 10^{-5}$M glyphosate, the inhibition of the mutated synthase will usually be less than about half, preferably less than a quarter of the inhibition of the synthase from the original strain.

The following examples are offered by way of illustration and not by way of limitation.

EXPERIMENTAL MATERIALS AND METHODS

Media and Bacterial Strains

The bacterial strains used are listed in Table 1.

TABLE 1

| Bacterial Strains | | |
|---|---|---|
| Designation | Pertinent genotype/ phenotype | Origin/reference |
| S. typhimurium | | |
| TA831 | aroA+ hisF645 | Ames |
| A1 | aroA1 | a |
| A124 | aroA124 | b |
| A148 | aroA148 | a |
| STK1 | aroA+ | P22TTA831xA1, this work |
| CTF3 | aroA+, Pmg$^r$ | P22TA831/EMSxA1, this work |
| CT7 | aroA+, Pmg$^r$ | P22CTF3/EMSxA1, this work |
| E. coli | | |
| HB101 | recA, hsdrR | B. Bachmann$^c$ |
| WA802 | hsdR2, hsdA+ | B. Bachmann |
| SK472 | serB22, zjj-202:Tn10 | S. Kushner |
| AB2829 | aroA hsdR+ | B. Bachmann |
| AB1321 | aroA hsdR+ | B. Bachmann |
| JF568 | aroA hsdR+ | B. Bachmann |
| LCK8 | hsdR2, zjj-202::Tn10 | P1SK472xWA802, this work |
| LC1 aroA | hsdR2, zjj-202::Tn10 | P1LCK8xJF568, this work |
| LC2 aroA | hsdR2, zjj-202::Tn10 | P1LCK8xAB1321, this work |
| LC3 aroA | hsdR2, zjj-202::Tn10 | P11LK8xAB2829, this work |
| NS428 | | d |
| NS433 | | d |

$^a$Nishioka et al., Genetics (1967) 56:341-351.
$^b$Gollub et al., J. Biol. Chem. (1967) 242:5323-5328.
$^c$Bachmann, E. coli Genetic Stock Center, Dept. of Human Genetics, Yale University, New Haven, Connecticut.
$^d$Enquist, L. & N. Sternberg, Meth. Enzymol., 1979, 281-298 (Academ. Pr., NY)

Selection and Testing for Glyphosate Resistance

Glyphosate was added to M9 medium after autoclaving. For selection experiments, a commercial solution of glyphosate was used. Resistant mutants were isolated by plating bacterial suspensions in M9 broth or on M9 solid medium supplemented with varying amounts of glyphosate. The level of resistance achieved by the mutants was scored by three types of tests: a spot test, consisting of toothpicking a small colony from a non-selective to a selective medium; a streak test, consisting of streaking cells on a selective plate to obtain single colonies; and growth curves, to determine the kinetics of growth in liquid medium supplemented with glyphosate.

DNA Transformation and Transduction of Packaged Cosmid DNA

DNA transformation was performed according to Mandel and Higa, J. Mol. Biol. (1970) 53:159-162. Competent cells were stored at −70° C. in 15% glycerol. Cells for transduction of packaged cosmid DNA were grown to late log phase in 1 ml of LB broth supplemented with 0.4% maltose. Cells were pelleted and resuspended in 0.1 ml of 10 mM $MgSO_4$ to which was added 20-100 μl of a packaged cosmid suspension. Phage particles were allowed to absorb to cells for 20 min. at 37° C. Transductants were allowed to express for one hour at 37° C. with aeration in 2 ml of LB broth and subsequently plated on selective medium. Using either type of packaging extract, $2 \times 10^5$ cosmids/μg of insert DNA were routinely obtained. Biotec preparations were rated at $10^8$ phages/μg of ligated native lambda DNA while the subject extracts were rated at $10^7$.

Enzyme Preparation and Assay for ES-3-P Synthase

*S. typhimurium* strains CT7 and STK1 were grown with aeration for 24 hours at 37° C. in M9 broth. Cells were harvested by centrifugation at 4° C., washed twice with M9 salts, resuspended in 0.01M Tris-HCL (pH8.2) and sheared with a French press at 20,000 psi. The homogenate was centrifuged at 16,000 g for 40 min and the supernatant treated with 2% protamine sulfate (1.0 ml of 2% protamine sulfate for every 35 mg of protein). The precipitate was removed by centrifugation at 18,000 $\times$ g for 35min, resuspended and used for enzyme assays. Activity of the enzyme was determined by measuring the rate of release of inorganic phosphate (Heinonen and Lahti, Anal. Biochem. (1981) 113:313–317).

A typical assay mixture contained 150 $\mu$mole maleic acid buffer (pH 5.6), 2.88 $\mu$mole phosphoenolpyruvate, 4.08 $\mu$mole 3-phosphoshikimate and the enzyme fraction in a total volume of 1.5 ml. The reaction was started by addition of the enzyme after pre-incubation of the assay mixture at 37° C. for 5 min. Aliquots were taken at timed intervals and mixed immediately with the reagents for phosphate analysis. The low pH of the reagent (1.25 N $H_2SO_4$) terminated enzyme activity.

RESULTS

Isolation of Glyphosate Resistant Mutants Mapping in the aroA Locus

*S. typhimurium* strain TA831 did not form colonies on solid M9 medium containing more than 200 $\mu$g/ml of glyphosate. For initial selection, the concentration of 350 $\mu$g/ml for screening glyphosate-resistant mutants was chosen. Spontaneous mutants appeared at a frequency of $5 \times 10^{-8}$ per cell plated. In none of ten independent mutants tested did glyphosate resistance cotransduce with aroA.

To improve the chances of finding aroA mutants chemical mutagenesis was employed, as well as an enrichment step in which glyphosate-resistant mutants mapping in aroA were selected on 350 $\mu$g/ml glyphosate by cotransduction. After mutagenesis of *S. typhimurium* strain TA831 with ethyl methanesulfonate, the frequency of glyphosate-resistant mutants was $1 \times 10^{-4}$ per cell plated. Two groups of 10,000 mutants originating from independent mutagenesis experiments were used to prepare a mixed lysate of P22. This was then used to transduce *S. typhimurium* strain A1. Cells were plated on M9 medium and M9 plus glyphosate. The number of colonies appearing on glyphosate plates was one hundredth of those appearing on M9 alone. None ($<10^{-3}$) appeared when a phage lysate from unmutagenized strain TA831 was used. Ten glyphosate-resistant mutants were tested and all cotransduced with aroA. These results suggest that about 1% of all mutations conferring glyphosate resistance mapped close to, or in, aroA. One of the mutants was chosen for further characterization and was designated strain CTF3. By a spot test it was resistant to 350 $\mu$g/ml of glyphosate. A second cycle of mutagenesis was carried out on strain CTF3 to obtain a higher level of resistance to glyphosate. Ten cultures were treated with ethyl methanesulfonate, and plated on 1 mg/ml of glyphosate. Resistant colonies appeared with a frequency of $10^{-6}$ per cell plated. Ten thousand mutants were again pooled for each mutagenesis group and lysates prepared from each pool used to transduce strain A1. Transductants were selected on M9 and M9-supplemented with 1 mg/ml glyphosate. Selection for aroA+ gave $10^{-5}$ transductants per cell plated. Selection for aroA+, glyphosate-resistant cells gave a transduction frequency of $10^{-8}$. In fifteen of twenty transductants tested glyphosate resistance cotransduced with aroA. From these results it was deduced that approximately $1 \times 10^{-3}$ mutations obtained in the mutagenesis of strain CTF3 mapped close, or in, the aroA locus. The phenotype expressed by these mutants is designated $Pmg^r$. No significant difference in resistance levels was detected among fifteen separate mutants. All formed colonies in 48 hours when streaked on M9 medium containing 2 mg/ml of glyphosate. Mutant CT7 was chosen for further characterization. $Pmg^r$ in this strain cotransduced 97–99% of the time with aroA1, aroA126 and aroA248.

Mechanisms of Glyphosate Resistance

Resistance to glyphosate mediated by a mutation(s) at the aroA locus could result from altered regulation leading to overproduction of 5-enolpyruvyl3-phosphoshikimate synthase or to a structural alteration of the enzyme. To distinguish between these two hypotheses in vitro enzyme preparations were assayed from Salmonella strains STK1 and CT7 which are the wild type and mutant strain respectively. 5-Enolpyruvyl-3-phosphoshikimate synthase activities from wild type and glyphosate-resistant mutants differed by Km for 3-phosphoshikimate, $K_d$ for glyphosate, and at high concentration of 3-phosphoshikimate, by specific activity. These results are summarized in Table 2.

TABLE 2[a]

| Source[c] | Specific activity[b] 3-P-shikimate, conc. M | | $K_m$ 3-P-shikimate | $K_d$ glyphosate |
|---|---|---|---|---|
| | $3.4 \times 10^4$ | $3.4 \times 10^{-3}$ | | |
| STK 1 | $0.7 \times 10^{-6}$ | $1.7 \times 10^{-6}$ | $3.4 \times 10^{-4}$ | $2.2 \times 10^{-5}$ |
| CT7 | $1.1 \times 10^{-6}$ | $3.7 \times 10^{-6}$ | $2.8 \times 10^{-3}$ | $1.9 \times 10^{-4}$ |

[a]Enzyme preparations were obtained as described in Materials and Methods. Phosphoenolpyruvate was $2.5 \times 10^{-1}$ M in all assays.
[b]Pi-ml$^{-1}$-sec.$^{-1}$-$\mu$g protein$^{-1}$.
[c]Cells of the wild type, STK1 and of the glyphosate-resistant mutant, CT7, were grown in minimal medium to early stationary phase.

The above assays were performed on enzyme preparations obtained from cells grown in minimal medium. To determine whether the enzyme of the glyphosate resistance mutant was differentially regulated during glyphosate induced stress, STK1, the wild type, and CT7 the mutant, were grown in minimal medium supplemented, respectively, with 70 $\mu$g/ml and 1000 $\mu$g/ml of glyphosate. These conditions give approximately 20–30% growth inhibition. The specific activity of preparations from cells grown in the presence of glyphosate was 10% higher than that found in preparations from cells grown without glyphosate. This increase in activity was exhibited both by STK1 and CT7 ruling out that in the glyphosate-resistant mutant, the enzyme would be overproduced in response to glyphosate.

The growth kinetics of both *S. typhimurium* and *E. coli* strains with wild type and mutant aroA locus were investigated. In minimal medium strains of either genus harboring the aroA -$Pmg^r$ allele only exhibited a 15% lower growth rate than the isogenic line harboring either the wild type allele, or both wild type and $Pmg^r$ alleles. At 100 $\mu$g/ml glyphosate, wild type *E. coli* showed 40% inhibition of growth rate. At one mg/ml glyphosate, no growth was observed. The aroA *E. coli* strain LC3 harboring pPMG1 (to be described subsequently) was not significantly inhibited at 2 μg/ml of glyphosate.

Cloning of the aroA and aroA Pmg$^r$ Locus

Chromosomal DNA from strain CT7 was partially digested with the restriction endonuclease Sau3A. pVK100, a low copy number, 23Kb cosmid vector (Knauf and Nester, Plasmid (1982) 8:45–54), was partially digested wth BglII to avoid excision of the cos site which is on a BglII fragment. Equal amounts of vector and insert DNA were mixed, ligated, and packaged in lambda capsids as described in Methods. Analysis of random transductants from the bank revealed that 60% of them harbored cosmid DNA of the expected size (45 Kb), consisting of the vector pVK100 and an average chromosomal insert of 20-25 Kb. To isolate the aroA-Pmg$^r$ gene E. coli aroA mutants were complemented. Due to the presence of Salmonella DNA the bank did not transduce hsdR+ strains of E. coli. Three E. coli strains were constructed which were both aroA and hsdR. For this purpose strain SK472 in which zjj202::Tn10 is linked to hsdR+ was used. By transducing zjj202::Tn10 in strain WA802 and selecting for tetracycline resistant, serine auxotrophic, restriction deficient recombinants, zjj202::Tn10 was linked to the hsdR2 allele. This was introduced into three different aroA mutants by selection for Tn10. The three new strains derived from JF568, AB1321 and AB2829 were, respectively, designated LC1, LC2 and LC3. LC3 was chosen for further experiments since it had the lowest aroA+ reversion rate. After transduction of the Salmonella CT7 DNA bank into strain LC3, 500 kanamycin resistant transductants were screened for growth on minimal medium. Two aroA+ clones were found. When tested for glyphosate resistance they were found to be as resistant as strain CT7. Plasmid DNA was isolated from these clones and both harbored a 45Kb cosmid which by preliminary restriction endonuclease analysis were found to be similar. One of the two plasmids (pPMG1) was chosen for further characterization.

When introduced by transformation into the appropriate E. coli strains, pPMG1 complemented all aroA mutations tested (see Table 1); in addition, it conferred glyphosate resistance to all strains into which it was introduced, either aroA or aroA+. By conjugation, using pRK2013 (Ditta et al., Proc. Natl. Acad. Sci. USA (1980) 77:7347-7351) as a mobilizing factor, pPMG1 was introduced into S. typhimurium strains A1, A124 and A148 where it conferred an aroA+ Pmg$^r$ phenotype. Enzymatic characterization of aroA+ E. coli transformants confirmed the phenotypic response, since ES-3-P synthase activity in these strains was indistinguishable from that in strain CT7. It was concluded that the aroA-Pmg$^r$ gene was cloned. The wild type aroA allele was also cloned using a similar protocol. Two cosmids were isolated from a bank of STK1 DNA. They carried a common region of approximately 10Kb and were designated pAROA1 and pAROA2.

To subclone the aroA-Pmg$^r$ gene, plasmid pPMG1 was digested with the restriction endonuclease BglII. Three insert fragments were found that were 10, 9.6 and 1.6Kb in size, respectively. Plasmid pPMG1 was digested to completion with BglII, ligated in vitro and the DNA transformed into strain LC2 selecting for aroA complementation. Clones were screened and plasmids containing the 10Kb BglII fragment in both orientations relative to the vector pVK100 were identified. Plasmids pPMG5 and pPMG6 complemented aroA E. coli strains and conferred high levels of glyphosate resistance. Further subcloning was accomplished by digesting plasmid pPMG5 with BglII and HindIII and ligating in vitro. Strain LC2 was transformed and colonies which were aroA+ and kanamycin sensitive were selected. Analysis of plasmids contained in these clones showed a 5.5 Kb BglII/HindIII Salmonella DNA segment that complements aroA E. coli strains and confers high levels of glyphosate resistance (approx. 2 mg/ml). This plasmid was designated pPMG11. An electrophoresis gel indicated that plasmids pPMG1, pPMG5 and pPMG11 as well as pAROA1 (a plasmid containing the wild type Salmonella aroA+ allele) all contain the 5.5 Kb BglII/HindIII DNA segment.

Preparation of Ti-plasmid Construct pPMG11 (see also Comai et al., Science (1983) 221:370) was digested with BglII and SalI and the BglII-SalI fragment substituted into BamHI-SalI digested pACYC184 (Chang and Cohen, J. Bacteriol. (1978) 134:114) to provide plasmid pPMG17. After cloning and isolation, pPMG17 was partially digested with HpaII and inserted into HpaII digested pUC9 (Vieira and Messing, Gene (1982) 19:259). After cloning and isolation, this plasmid was digested with HindIII, followed by Ba131 resection, addition of BamHI linkers and ligation to provide plasmid pPMG34, a plasmid of about 3.6 kb, approximately 0.6 kb smaller than pPMG31. The aroA gene is now flanked by BamHI restriction sites. pPMG34 was digested with BamHI and inserted into BamHI digested pUC7 (Vieira and Messing, supra) to provide after cloning and isolation pPMG38, 3.6 kb, where the aroA gene is flanked by EcoRI restriction sites.

pPMG38 was digested with EcoRI to provide a fragment including the entire aroA gene with the 3' untranslated flanking region including a fragment from pACYC184, followed by a fragment from pUC7, while the 5'-region is as described below:

| pUC7 | BamHI Linker | aroA sequence | 0 |
|---|---|---|---|
| GAATTCCCCG | GATCCC | GTTTCTGTTTTTTGAGAGTTGAGTTTGATG | |

The aroA fragment described above was inserted into the EcoRI site of pCGN451.

pCGN451 includes an octopine cassette which contains about 1,566 bp of the 5' non-coding region fused via an EcoRI linker to the 3' end of the gene and about 1,349 bp of 3' non-coding DNA. The pTi coordinates are 11,207 to 12,823 for the 3' region and 13,643 to 15,208 at the 5' region as defined by Borker et al., Plant Molecular Biology (1983) 2:335. The 5' fragment was obtained as follows: A small subcloned fragment containing the 5' end of the coding region, as a BamHI-EcoRI fragment was cloned in pBR322 as plasmid pCGN407. The BamHI-EcoRI fragment has an XmnI site in the coding region, while pBR322 has two XmnI sites. pCGN407 was digested with XmnI, resected with Ba131 nuclease and EcoRI linkers added to the fragments. After EcoRI and BamHI digestion, the fragments were size fractionated, the fractions cloned and sequenced. In one case, the entire coding region and 10 bp of the 5' non-translated sequences had been removed leaving the 5' non-transcribed region, the mRNA cap site and 16 bp of the 5' non-translated region (to a BamHI site) intact. This small fragment was obtained by size fractionation on a 7% acrylamide gel and fragments approximately 130 bp long eluted. This size fractionated DNA was ligated into M13mp9 and several clones sequenced and the sequence compared to the known sequence of the octopine synthase gene. The M13 construct was designated pI4, which plasmid was digested with BamHI and EcoRI to provide the small fragment which was ligated to an XhoI to BamHI fragment containing upstream 5' sequences from pTiA6 (Garfinkel and Nester, *J. Bacteriol.* (1980) 144:732) and to an EcoRI to XhoI fragment containing the 3' sequences. The resulting XhoI fragment was cloned into the XhoI site of a pUC8 derivative, designated pCGN426. This plasmid differs from pUC8 by having the sole EcoRI site filled in with DNA polymerase I, and having lost the PstI and HindIII site by nuclease contamination of HincII restriction endonuclease, when a XhoI linker was inserted into the unique HincII site of pUC8. The resulting plasmid pCGN451 has a single EcoRI site for the insertion of protein coding sequences between the 5' non-coding region (which contains 1,550 bp of 5' non-transcribed sequence including the right border of the T-DNA, the mRNA cap site and 16 bp of 5' non-translated sequence) and the 3' region (which contains 267 bp of the coding region, the stop codon, 196 bp of 3' non-translated DNA, the polyA site and 1,153 bp of 3' non-transcribed sequence).

The XhoI fragment containing the octopine synthetase (ocs) cassette was inserted into plasmid pCGN517, which has tetracycline resistance and kanamycin resistance genes. pCGN517 was prepared from pHC79 (Hohn, *Gene* (1980) 11:291) by introducing into the unique PstI site, the Kan$^r$ gene from pUC4K (Vieira, *Gene* (1982) 19:259). pCGN517 was digested with SalI and the XhoI fragment inserted into the unique SalI site.

The XhoI fragment was also inserted into a second plasmid pCGN529. pCGN529 is prepared from pACYC184 by insertion of the Kan$^r$ gene from Tn5 (Rothstein et al., 1981, in *Movable Genetic Elements*, p. 99, Cold Spring Harbor Laboratories, Cold Spring Harbor, N.Y.) and a BglII fragment of 2.4 kb from pRiA4 T-LDNA (White and Nester, *J. Bacteriol.* (1980) 144:710) inserted into the BamHI site remaining after substitution of the HindIII-BamHI fragment of pACYC184 with the Kan$^r$ gene of Tn5.

The XhoI fragment from pPMG45 containing the ocs cassette with the EcoRI aroA fragment inserted at the unique EcoRI site of the ocs cassette inserted into pCGN517 and pCGN529 gave pPMG54 and pPMG55, respectively. These plasmids could then be used for introduction into *A. tumefaciens* or *A. rhizogenes*, respectively, for integration to the T-DNA of the Ti- or Ri-plasmids. Integration into the respective plasmids was achieved in a three-way mating as described by Comai et al., *Plasmid* (1983) 10:21–30. Overnight cultures of *E. coli* host containing plasmids pRK2073, pPMG54 or pPMG55, and *A. tumefaciens* A722 (Garfinkel, *J. Bacteriol.* (1980) 144:732) or *A. rhizogenes* A4T (White, ibid. (1980) 144:710) were cultured overnight and the appropriate cultures mixed and spread on AB plates containing 150 μg/ml kanamycin. Single colonies were restreaked twice. Correct integration was verified by Southern analysis of total Agrobacterium DNA. HindIII, BamHI and XhoI digested DNA was probed with a nick-translated pPMG38. Southern analysis and nick-translation were performed as described (Maniatis et al. (1982) *Molecular Cloning*, Cold Spring Harbor Press, Cold Spring Harbor, N.Y.).

Transformation and regeneration of tobacco leaf slices cocultivated with *A. rhizogenes*.

Tobacco plants are cultivated axenically (25° C., white light (16 hr); MS (1 mg/L IAA, 0.15 mg/L kinetin). Three-week-old plants maintained through main shoot transplant are used as tissue donors. Young leaves (down to the fourth from the top) are selected, leaf disks 2 mm in diameter are punched out and placed in Petri dishes (3 cm in diameter) in 1 ml of MS medium with 1 mg/L IAA. After keeping the disks overnight in total darkness, Agrobacterium cells ($10^8$–$10^9$ /ml in plant culture medium) are added to these cultures. Co-cultivation is carried out for 18–24 hr in darkness. Leaf slices are freed from Agrobacterium by washing 3× with MS medium lacking hormones and containing 350 mg/L cefotaxine (Boehringer-Mannheim). Leaf slices are transferred in 9 cm Petri dishes in 10 ml of MS medium without hormones. Phytagar (Gibco, 0.6%; cefotaxine, 350 mg/L) Petri dishes are sealed with parafilm and kept under the same conditions as tissue donor plants. Roots appear up to 2-4 weeks, are excised and placed under the same conditions in the same medium plus 2 mg/L IAA and 2 mg/L kinetin. Regenerating shoots are visible in the following 2–5 weeks.

RESULTS

In the first study glyphosate inhibition of transformed *Nicotiana tobacum* "Xanthi" was studied. Plants were sprayed at the six-leaves stage by directing a spray of Roundup (glyphosate) solution toward the potted plant. Each four-inch pot contained a plant and received 2.5 ml of spray. Given the surface area of the pot, milligrams of glyphosate/pot are equivalent to pounds/acre. Plants were grown in a growth chamber at 25° C., 70% relative humidity, 60 hr light period. Growth was scored 9 days after spraying by counting the new leaves longer than 0.5 cm. The values for three control plants and four aroA+ plants are given for each glyphosate rate. The following Table 3 indicates the results.

TABLE 3

| Inhibition by glyphosate of transformed *Nicotiana tabacum* "Xanthi" expressing the aroA protein.[a] | | |
|---|---|---|
| Glyphosate[b] mg/pot lbs/acre | Apical Shoot Growth[c] Control (A4T) | (# of leaves since spraying) aroA+ (A4T-55) |
| 0 | 4, 4, 3; | 3, 6, 6, 6; |
| 0.5 | 1, 0, 0; | 3, 4, 4, 3; |
| 1.25 | 0, 0, 0; | 1, 0, 0, 0; |

[a]Plants were regenerated from *Agrobacterium rhizogenes* transformed roots. A4T contains wild type pRiA4 plasmid. A4T-55 contains pRiA4-55, a chimeric derivative of pRiA4 carrying the ocs-aroA construct.
[b]Plants were sprayed at the six leaves stage, by directing a spray of Roundup (glyphosate) solution toward the potted plant. Each four inch pot contained a plant and received 2.5 ml of spray. Given the surface area of the pot mg of glyphosate/pot are equivalent to lbs/acre. Plants were grown in growth chamber at 25° C., 70% relative humidity, 16 hours light period.
[c]Growth was scored nine days after spraying by counting the new leaves longer than 0.5 cm. The values for three control plants and four aroA + plants are given for each glyphosate rate.

In the next study, a comparison of the kinetic parameters at pH 7.0 of ES-3-P synthase purified from wild-type *S. typhimurium* and from the mutant glyphosate-resistant strain was made. Enzyme activity was assayed fluorometrically in the forward direction as described by Boocock and Coggins, *FEBS Letters* (1983) 154:127–133.

TABLE 4

Comparison of the kinetic parameters at pH 7.0 of EPSP synthase purified from wild type *S. typhimurium* and from the mutant glyphosate-resistant strain. Enzyme activity was assayed fluorimetrically in the forward direction as described by Boocock and Coggins.

| Kinetic Parameter | Wild Type | Mutant |
|---|---|---|
| Km for shik 3-P* | 2.6 μM (500 μM PEP)** | 1.6 μm (500 μM PEP) |
| Km for PEP | 30 μM (500 μM shik 3-P) | 22 μM (500 μM shik 3-P) |
| Ki for glyphosate | 1.5 μM (500 μM shik 3-P) | 5.0 μM (500 μM shik 3-P) |

*shik 3-P = 3-phosphoshikimic acid
**PEP = phosphoenolpyruvate

In the next study, the effect of glyphosate and antiserum to bacterial EPSP synthate on EPSP synthase activities from the glyphosate-resistant strain of *S. typhimurium*, from wild-type turnip gall and from ocs-aroA turnip gall was studied. Enzyme activity was assayed fluorometrically in the forward direction as described by Boocock and Coggins, supra.

TABLE 5

The effect of glyphosate and anti-serum to bacterial EPSP synthase activities from the glyphosate-resistant strain of *S. typhimurium*, from wild type turnip gall, and from ocs-aroA transformed turnip gall. Enzyme activity was assayed fluorimetrically in the forward direction as described by Boocock and Coggins.

| | EPSP Synthase Activity, % control[a] | | |
|---|---|---|---|
| Inhibitor | Bacterial Mutant[b] | Wild Type Turnip Gall | ocs-aroA Turnip Gall |
| None | 100 | 100 | 100 |
| Glyphosate | | | |
| 100 μM | 35 | 8 | 29 |
| 500 μM | 9 | 2 | 9 |
| Antiserum to bacterial EPSP synthase[c] | 1 | 115 | 42 |

[a]Assayed at pH 7.0; PEP = 500 μM; shik 3-P = 500 μM
[b]Measured in a mixture of purified bacterial enzyme with an amount of wild type turnip gall crude extract equivalent to that used on the turnip gall assays.
[c]Each extract was pre-incubated with antiserum for 10 minutes at 0° C. before assay.

To further establish the presence of the mutated bacterial aroA gene being present in plants, Western blot detection of the aroA expression product was performed as described in Burnette, *Anal. Biochem.* (1981) 112:195. Comparison of the Western blot from the various plants described above with authentic aroA protein demonstrated the presence of the aroA expression product in each of the transformed plants.

The following table indicates the complete DNA sequence of the wild-type *S. typhimurium* aroA gene, with the box indicating the single substitution providing for glyphosate resistance.

```
                                  1400
TTTCTGTTTTTTGAGAGTTGAGTTTC  ATG  GAA  TCC  CTG  ACG  TTA  CAA  CCC
                            Met  Glu  Ser  Leu  Thr  Leu  Gln  Pro

1450
ATC  GCG  CGG  GTC  GAT  GGC  GCC  ATT  AAT  TTA  CCT  GGC  TCC  AAA  AGT
Ile  Ala  Arg  Val  Asp  Gly  Ala  Ile  Asn  Leu  Pro  Gly  Ser  Lys  Ser
                                    Ala                                  Thr
                                    17

1500
GTT  TCA  AAC  CGT  GCT  TTG  CTC  CTG  GCG  GCT  TTA  CCT  TGT  GGT  AAA
Val  Ser  Asn  Arg  Ala  Leu  Leu  Leu  Ala  Ala  Leu  Ala  Cys  Gly  Lys
                                                            His

1550
ACC  GCT  CTG  ACG  AAT  CTG  CTG  GAT  AGC  GAT  GAC  GTC  CGC  CAT  ATG
Thr  Ala  Leu  Thr  Asn  Leu  Leu  Asp  Ser  Asp  Asp  Val  Arg  His  Met
     Val
     40

1600
CTC  AAT  GCC  CTG  AGC  GCG  TDG  GGG  ATC  AAT  TAC  ACC  CTT  TCT  GCC
Leu  Asn  Ala  Leu  Ser  Ala  Leu  Gly  Ile  Asn  Tyr  Thr  Leu  Ser  Ala
                                        Val  Ser
                                             63

1650
GAT  CGC  ACC  GCG  TGT  GAT  ATC  ACG  GGT  AAT  GGC  GGC  GCA  TTA  CGT
Asp  Arg  Thr  Arg  Cys  Asp  Ile  Thr  Gly  Asn  Gly  Gly  Ala  Leu  Arg
                         Glu       Ile                      Pro       His

GCG  CCA  GGC  GCT  CTG  GAA  CTG  TTT  CTC  GGT  AAT  GCC  GGA  ACC  GCG
Ala  Pro  Gly  Ala  Leu  Glu  leu  Phe  Leu  Gly  Asn  Ala  Gly  Thr  Ala
     Glu  86
```

|  | 1700 | T |  |  |  |  |  |  |  |  |  |  |  |  |
|---|---|---|---|---|---|---|---|---|---|---|---|---|---|---|
| ATG | CGT | CCG | TTA | GCG | GCA | GCG | CTA | TGT | CTG | GGG | CAA | AAT | GAG | ATA |
| Met | Arg | Pro | Leu | Ala | Ala | Ala | Leu | Cys | Leu | Gly | Gln | Asn | Glu | Ile |
|  |  | Ser |  |  |  |  |  |  |  |  |  |  |  |  |

|  |  | 1750 |  |  |  |  |  |  |  |  |  |  |  |  |
|---|---|---|---|---|---|---|---|---|---|---|---|---|---|---|
| GTG | TTA | ACC | GGC | GAA | CCG | CGT | ATG | AAA | GAG | CGT | CCG | ATA | GGC | CAT |
| Val | Leu | Thr | Gly | Glu | Pro | Arg | Met | Lys | Glu | Arg | Pro | Ile | Gly | His |

|  |  |  |  | 1800 |  |  |  |  |  |  |  |  |  |  |
|---|---|---|---|---|---|---|---|---|---|---|---|---|---|---|
| CTG | GTC | GAT | TCG | CTG | CGT | CAG | GGC | GGG | GCG | AAT | ATT | GAT | TAC | CTG |
| Leu | Val | Asp | Ser | Leu | Arg | Gln | Gly | Gly | Ala | Asn | Ile | Asp | Tyr | Leu |
|  |  |  | Ala |  |  | Leu |  |  |  | Lys |  | Thr |  |  |
|  |  |  | 133 |  |  |  |  |  |  |  |  |  |  |  |

|  |  |  |  |  | 1850 |  |  |  |  |  |  |  |  |  |
|---|---|---|---|---|---|---|---|---|---|---|---|---|---|---|
| GAG | CAG | GAA | AAC | TAT | CCG | CCC | CTG | CGT | CTG | CGC | GGC | GGT | TTT | ACC |
| Glu | Gln | Glu | Asn | Tyr | Pro | Pro | Leu | Arg | Leu | Arg | Gly | Gly | Phe | Try |
|  |  |  |  |  |  |  |  |  |  | Gln |  |  |  |  |
|  |  |  |  |  |  |  |  |  |  |  | 145 |  |  |  |

|  |  |  |  |  |  | 1900 |  |  |  |  |  |  |  |  |
|---|---|---|---|---|---|---|---|---|---|---|---|---|---|---|
| GGC | GGC | GAC | ATT | GAG | GTT | GAT | GGT | AGC | GTT | TCC | AGC | CAG | TTC | CTG |
| Gly | Gly | Asp | Ile | Glu | Val | Asp | Gly | Ser | Val | Ser | Ser | Gln | Phe | Leu |
|  |  | Asn |  | Val | Asp |  |  |  |  |  |  |  |  |  |

|  |  |  |  |  |  |  |  |  | 1950 |  |  |  |  |  |
|---|---|---|---|---|---|---|---|---|---|---|---|---|---|---|
| ACC | GCT | CTG | CTG | ATG | ACG | GCG | CCG | CTG | GCC | CTC | AAA | GAC | ACA | ATT |
| Thr | Ala | Leu | Leu | Met | Thr | Ala | Pro | Leu | Ala | Pro | Lys | Asp | Thr | Ile |
|  |  |  |  |  |  |  |  |  |  |  | Glu |  |  | Val |
|  |  |  |  | 179 |  |  |  |  |  |  |  |  |  |  |

|  |  |  |  |  |  |  |  |  |  | 2000 |  |  |  |  |
|---|---|---|---|---|---|---|---|---|---|---|---|---|---|---|
| ATT | CGC | GTT | AAA | GGC | GAA | CTG | GTA | TCA | AAA | CCT | TAC | ATC | GAT | ATG |
| Ile | Arg | Val | Lys | Gly | Glu | Leu | Val | Ser | Lys | Pro | Tyr | Ile | Asp | Ile |
|  |  | Ile |  |  | Asp |  |  |  |  |  |  |  |  |  |
|  |  |  |  |  |  |  |  |  |  |  |  | 202 |  |  |

|  |  |  |  |  |  |  |  |  |  |  | 2050 |  |  |  |
|---|---|---|---|---|---|---|---|---|---|---|---|---|---|---|
| ACG | CTA | AAT | TTA | ATG | AAA | ACC | TTT | GGC | GTG | GAG | ATA | GCG | AAC | CAC |
| Thr | Leu | Asn | Leu | Met | Lys | Thr | Phe | Gly | Val | Glu | Ile | Ala | Asn | His |
|  |  |  |  |  |  |  |  |  |  |  |  | Glu |  | Gln |

|  |  |  |  |  |  |  |  |  |  |  |  |  |  | 2100 |
|---|---|---|---|---|---|---|---|---|---|---|---|---|---|---|
| CAC | TAC | CAA | CAA | TTT | GTC | GTG | AAG | GGA | GGT | CAA | CAG | TAT | CAC | TCT |
| His | Tyr | Gln | Gln | Phe | Val | Val | Lys | Gly | Gly | Gln | Gln | Tyr | His | Ser |
|  |  |  |  |  |  |  |  |  |  |  | Ser |  | Gln |  |
|  |  |  |  |  | 225 |  |  |  |  |  |  |  |  |  |

|  |  |  |  |  |  |  |  |  |  |  |  |  |  |  |
|---|---|---|---|---|---|---|---|---|---|---|---|---|---|---|
| CCA | GGT | CGC | TAT | CTG | GTC | GAG | GGC | GAT | GCC | TCG | TCA | GCG | TCC | TAT |
| Pre | Gly | Arg | Tyr | Leu | Val | Glu | Gly | Asp | Ala | Ser | Ser | Ala | Ser | Tyr |
|  |  | Thr |  |  |  |  |  |  |  |  |  |  |  |  |
|  |  |  |  |  |  |  |  |  |  |  |  |  | 248 |  |

|  | 2150 |  |  |  |  |  |  |  |  |  |  |  |  |  |
|---|---|---|---|---|---|---|---|---|---|---|---|---|---|---|
| TTT | CTC | GCC | GCT | GGG | GCG | ATA | AAA | GGC | GGC | ACG | GTA | AAA | GTG | ACC |
| Phe | Leu | Ala | Ala | Gly | Ala | Ile | Lys | Gly | Gly | Thr | Val | Lys | Val | Thr |
|  |  |  |  | Ala |  |  |  |  |  |  |  |  |  |  |

|  |  | 2200 |  |  |  |  |  |  |  |  |  |  |  |  |
|---|---|---|---|---|---|---|---|---|---|---|---|---|---|---|
| GGA | ATT | GGC | CGC | AAA | AGT | ATG | CAG | GGC | GAT | ATT | CGT | TTT | GCC | GAT |
| Gly | Ile | Gly | Arg | Lys | Ser | Met | Gln | Gly | Asp | Ile | Arg | Phe | Ala | Asp |
|  |  |  | Asn |  |  |  |  |  |  |  |  |  |  |  |
|  |  |  | 271 |  |  |  |  |  |  |  |  |  |  |  |

```
                         2250
GTG CTG GAG AAA ATG GGC GCG ACC ATT ACC TGG GGC GAT GAT TTT
Val Leu Glu Lys Met Gly Ala Thr Ile Thr Trp Gly Asp Asp Phe
                                    Cys                     Tyr
                                                            294

2300
ATT GCC TGC ACG CGC GGT GAA TTG CAC GCC ATA GAT ATG GAT ATG
Ile Ala Cys Thr Arg Gly Glu Leu His Ala Ile Asp Met Asp Met
    Ser                         Asn

2350
ACC CAT ATT CCG GAT GCG GCG ATG ACG ATT GCC ACC ACG GCG CTG
Asn His Ile Pro Asp Ala Ala Met Thr Ile Ala Thr Thr Ala Leu
                             317                     Ala

2400
TTT GCG AAA GGA ACC ACG ACG TTG CGC AAT ATT TAT AAC TGG CGA
Phe Ala Lys Gly Thr Thr Thr Leu Arg Asn Ile Tyr Asn Trp Arg
                        Arg

2450
GTG AAA GAA ACC GAT CGC CTG TTC GCG ATG GCG ACC GAG CTA CGT
Val Lys Glu Thr Asp Arg Leu Phe Ala Met Ala Thr Glu Leu Arg
340

2500
AAA GTG GGC GCT GAA GTC GAA GAA GGG CAC GAC TAT ATT CGT ATC
Lys Val Gly Ala Glu Val Glu Glu Gly His Asp Tyr Ile Arg Ile
                                363

2550
ACG CCG CCG GCG AAG CTC CAA CAC GCG GAT ATT GGC ACG TAC AAC
Thr Pro Pro Ala Lys Leu Gln His Ala Asp Ile Gly Thy Thy Asn
            Glu         Asn Phe     Glu     Ala

GAC CAC CGT ATG GCG ATG TGC TTC TCA CTG GTC GCA CTG TCC GAT
Asp His Arg Met Ala Met Cys Phe Ser Leu Val Ala Leu Ser Asp
    396

2600
ACG CCA GTT ACG ATC CTG GAC CCT AAA TGT ACC GCA AAA ACG TTC
Thr Pro Val Thr Ile Leu Asp Pro Lys Cys Thr Ala Lys Thr Phe
                                    409

2650
CCT GAT TAT TTC GAA CAA CTG GCG CGA ATG AGT ACG CCT GCC TAA
Pro Asp Tyr Phe Glu Gln Leu Ala Arg Met Ser Thr Pro Ala End
                                    Ile     Gln Ala

2700
                                    GTCTTCTGTTGCGCCAGTCGAC
```

In accordance with the subject invention, herbicidal resistance can be imparted to a sensitive host to provide for enhanced protection of the cells of the host. In addition, mutant enzymes can be produced which can find utility in a wide variety of situations involving enzymes as labels, for the measurement of various compounds, as well as for the production of products, where the enzyme may be free of inhibition from contaminants which inhibit or interfere with the enzyme catalyzed reaction. In addition, DNA sequences are provided which can be used for probing both wild type and mutated genes expressing ES-3-P synthase. Furthermore, a method is provided demonstrating a technique for mutating an enzyme in order to modify a selectable property and obtaining genes expressing such an enzyme.

Furthermore, the subject mutated genes are found to be expressed in plants and impart glyphosate resistance to plants. Thus, plants can be grown which will be protected from the herbicide glyphosate, which may then be used to kill weeds and prevent weeds from competing with the crops for space and nutrients, so as to greatly enhance the utilization of fertilizers and the growth of the desired crop.

Although the foregoing invention has been described in some detail by way of illustration and example for purposes of clarity of understanding, it will be obvious that certain changes and modifications may be practiced within the scope of the appended claims.

What is claimed is:

1. A method for producing glyphosateresistant 5-enolpyruvyl3-phoshoshikimate synthase which comprises:

growing a prokaryotic host containing a glyphosate-resistant 5-enolpyruvyl-3-phoshoshikimate synthase gene having at least one mutation originating from in vitro mutation in the aroA locus in an appropriate nutrient medium; and lysing said prokaryotic host and isolating said synthase.

2. A plant entity consisting essentially of a plant cell, seed, or plant having a gene, as a result of the in vitro introduction of said gene into a plant cell, said gene encoding for a mutated glyphosate resistant 5-enolpyruvyl-3-phosphoshikimate synthase enzyme, said gene being under the transcriptional control of regulatory signals functional in said plant entity, which said regulatory signals comprise plant derived transcriptional initiation regulatory signals, wherein when said plant entity is other than a cell, said plant entity is a dicotyledon.

3. A plant cell, seed or plant according to claim 2, wherein said plant cell into which said gene is introduced is Brassica.

4. A plant cell, seed or plant according to claim 2, wherein said plant cell into which said gene is introduced is Nicotiana.

5. A plant cell, seed or plant according to claim 2, wherein said gene is heterologous to said plant cell in which said gene is introduced.

6. A plant seed according to claim 2.

7. A plant cell having a gene encoding for a mutated glyphosphate resistant 5-enopyruvyl-3-phosphoshikimate synthase enzyme, said gene being heterologous to said plant cell and under the transcriptional control of regulatory signals functional in said plant cell.

8. A plant cell according to claim 7, wherein said regulatory signals comprise plant transcriptional initiation regulatory signals.

9. A method for improving crop growth which comprises:

applying to a field containing a dicotyledon crop having planted crop seeds or plants, which are glyphosate resistant due to having a mutated expressable gene encoding for glyphosate resistant 5-enolpyruvyl-3-phosphoshikimate synthase enzyme originally resulting from introduction into cells of said plants, a sufficient amount of glyphosate to control weed growth without significantly affecting crop growth.

10. A method according to claim 9, wherein said gene is derived from a prokaryotic gene.

11. A method according to claim 9, wherein included with said glyphosate is a second herbicide.

12. A method according to claim 11, wherein said second herbicide is alachlor, metachlor, 2,4 D type, bentazon, bromoxynil, atrazine, cyanazine, or aciflurofen.

* * * * *

UNITED STATES PATENT AND TRADEMARK OFFICE
CERTIFICATE OF CORRECTION

PATENT NO. : 4,769,061
DATED : September 6, 1988
INVENTOR(S) : Luca Comai

It is certified that error appears in the above-indentified patent and that said Letters Patent is hereby corrected as shown below:

Column 21, Claim 1, line 1, "glyphosateresistant" should be --glyphosate-resistant--.
Column 21, Claim line 2, "enolpyruvyl3-phosphoshikimate" should be--enolpyruvyl-3-phosphoshikimate--.
Column 22, Claim 7, line 2, "glyphosphate" should be--glyphosate--.
Column 22, Claim 7, lines 2-3, "5-enopyruvyl-3-phosphoshikimate" should be--5-enolpyruvyl-3-phosphoshikimate--.
Column 22, Claim 12, line 2, "metachlor" should be -- metalochlor--.

Signed and Sealed this

Thirteenth Day of December, 1994

Attest:

BRUCE LEHMAN

Attesting Officer

Commissioner of Patents and Trademarks